United States Patent [19]

Wu et al.

[11] 3,935,199

[45] Jan. 27, 1976

[54] IMINOMETHYLINDOLINES

[75] Inventors: Yao Hua Wu; Walter G. Lobeck, both of Evansville, Ind.

[73] Assignee: Mead Johnson & Company, Evansville, Ind.

[22] Filed: May 13, 1974

[21] Appl. No.: 469,201

Related U.S. Application Data

[62] Division of Ser. No. 253,672, May 8, 1972, Pat. No. 3,823,136, which is a division of Ser. No. 862,915, Oct. 1, 1969, Pat. No. 3,679,692.

[52] U.S. Cl...... 260/243 R; 260/309.6; 260/326.11; 260/295 C; 424/246; 260/244 R
[51] Int. Cl.² ..................................... C07D 279.04
[58] Field of Search......... 260/243 R, 326.11, 309.6

[56] References Cited
UNITED STATES PATENTS

| | | | |
|---|---|---|---|
| 2,872,453 | 2/1959 | Jacob et al. | 260/293 |
| 2,937,173 | 5/1960 | Shapiro et al. | 260/249.9 |
| 3,697,553 | 10/1972 | Wu et al. | 260/326.11 |
| 3,833,574 | 9/1974 | Haugwitz et al. | 260/243 R |

*Primary Examiner*—John M. Ford
*Attorney, Agent, or Firm*—Robert E. Carnahan; Robert H. Uloth

[57] ABSTRACT

This invention relates to a series of 1-iminomethylindolines which are analeptic agents capable of counteracting central nervous system depressant effects of pentobarbital and chloral hydrate. They also exhibit analgesic effects. This invention also relates to a process for the preparation of 1-iminomethylindolines which comprises reaction of an indoline with carboxamides selected from the group consisting of amides, lactams, symmetrical or unsymmetrical ureas and hydrazides. Typical examples of 1-iminomethylindoline derivatives are 5-acetyl-1-[2-(1-pyrrolinyl)]indoline and 1-[2-(5,5-dimethyl-1-pyrrolinyl)]indoline.

4 Claims, No Drawings

IMINOMETHYLINDOLINES

CROSS REFERENCE TO RELATED APPLICATIONS

This application is a division of U.S. application Ser. No. 253,672 filed May 8, 1972 and now U.S. Pat. No. 3,823,136 patented July 9, 1974, which in turn is a division of U.S. application Ser. No. 862,915 filed Oct. 1, 1969, now U.S. Pat. 3,679,692 patented July 25, 1972.

SUMMARY OF THE INVENTION

The compounds of the present invention relate to 1-iminomethyl derivatives of indolines of Formula I and the pharmaceutically acceptable acid addition salts thereof.

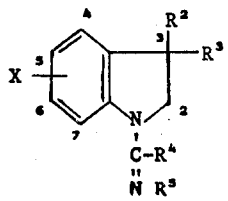

Formula I

These compounds which are new compositions of matter are characterized by Formula I and are useful as analeptic and analgesic agents in mammals.

In Formula I, the indoline ring positions are numbered to serve as an illustration of the numbering system employed herein for nomenclature purposes. The aromatic portion of the indoline ring in Formula I may be substituted in any of the 4, 5, 6, or 7 positions with an X grouping selected from the group consisting of hydrogen, nitro, amino, $R^1CO$, $R^1CONH$, and $R^1SO_2NH$. $R^1$ substituents represent a lower alkyl group of from 1 to 4 carbon atoms inclusive. The 3 position of the indoline ring may have $R^2$ and $R^3$ substituents independently selected from the group consisting of hydrogen and lower alkyl of from 1 to 3 carbon atoms inclusive. By independently selected it is meant that the $R^2$ and $R^3$ substituents may or may not be identical. An iminomethyl grouping represented by the symbol

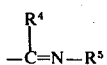

is attached to the 1 position of the indoline ring in Formula I. As employed herein the iminomethyl grouping is synonymous with the formimidoyl nomenclature used for this group by Chemical Abstracts. In the iminomethyl grouping, $R^4$ is selected from the group consisting of hydrogen, lower alkyl of from 1 to 4 carbon atoms inclusive, and $R^1NH$. In the case of $R^1NH$, the $R^1$ substituent of the 1-iminomethyl grouping is selected from the group consisting of lower alkyl of from 1 to 4 carbon atoms inclusive, cycloalkyl of from 4 through 7 carbon atoms such as cyclobutyl, cyclopentyl, cyclohexyl and cycloheptyl. The $R^5$ substituent is a lower alkyl having one to four carbon atoms inclusive. Also, $R^5$ can be pyrrolidinyl, piperdinyl as well as

wherein $R^6$ and $R^7$ are lower alkyl groups of 1 to 4 carbon atoms inclusive. In addition, $R^4$ and $R^5$ may be joined together to form, in combination with the atoms to which they are each attached a nitrogen containing cyclic compound selected from the group consisting of a heteromonocycle and heterobicycle being substituted with zero to two alkyl groups inclusuive having 1 through 4 carbon atoms inclusive and having from zero to one additional heteroatom selected from the group consisting of oxygen, nitrogen, and sulfur.

The term "lower alkyl" as employed herein includes both straight and branched chain radicals of the designated number of carbon atoms. For example, $R^1$ in the acyl grouping represented by $R^1CO$ and in the amido grouping $R^1CONH$ may be methyl, ethyl, propyl, isopropyl, 1-butyl, 1-methylpropyl, 2-methylpropyl, tert.-butyl. In the case where the X substituent is $R^1SO_2NH$, representative alkanesulfonamido groupings are 1-butanesulfonamido, 1-methylpropanesulfonamido, tert.-butanesulfonamido, methanesulfonamido, ethanesulfonamido, 1-propanesulfonamido, 2-propanesulfonamido. Alkyl groups which exemplify $R^2$ and $R^3$ substituents are methyl, ethyl, propyl, isopropyl. Inasmuch as the $R^2$ and $R^3$ groupings are independently selected from the group consisting of hydrogen and lower alkyl groupings, they may be identical or may be any combination thereof.

A particularly preferred embodiment of the present invention comprises compounds of Formula I, wherein X is located at the 5 position of the indoline ring and is selected from the group consisting of hydrogen, nitro, and $R^1CO$ wherein $R^1$ is a lower alkyl group of from 1 to 4 carbon atoms inclusive; $R^2$ and $R^3$ represent hydrogen; $R^4$ and $R^5$ are joined together to form in combination with the atoms to which they are each attached, a nitrogen containing heteromonocycle having 5 to 7 ring atoms; said heteromonocycle being substituted with zero to two alky groups having 1 to 4 carbon atoms inclusive; and the non-toxic, pharmaceutically acceptable acid addition salts thereof.

A more limiting and preferred embodiment of the present invention comprises the individual compounds 5-acetyl-1-[2-(1-pyrrolinyl)]indoline and 1-[2-(5,5-dimethyl-1-pyrrolinyl)]indoline.

The term pharmaceutically acceptable acid addition salts is construed to mean a combination of compounds of the present invention with relatively non-toxic inorganic and organic acids. In this respect, a variety of acids may be used and include sulfuric, phosphoric, hydrochloric, hydrobromic, hydroiodic, sulfamic, benzenesulfonic, methanesulfonic, para-toluenesulfonic, acetic, lactic, succinic, maleic, tartaric, citric, gluconic, ascorbic, benzoic, cinnamic, and related acids.

Conversion of the compounds of the present invention to corresponding pharmaceutically acceptable acid addition salts is accomplished by admixture of these compounds with substantially one chemical equivalent of any of the various acids hereinbefore defined in an inert organic solvent such as ethanol, benzene, ethyl acetate, ether, halogenated hydrocarbon and the like.

For pharmaceutical purposes, the compounds of this invention may be administered to mammals in the form of the free bases or in the form of one of their non-toxic acid addition salts. In either form the compounds of Formula I may be compounded and formulated into pharmaceutical compositions of unit dosage form suitable for systemic administration with organic or inorganic solid materials or liquids which are pharmaceutically acceptable carriers. By systemic administration it is meant such form of administration as oral, parenteral and rectal. Pharmaceutical compositions considered within the scope of this invention may take the form of tablets, powder, granulas, capsules, suspensions, solutions, suppositories, elixirs, ointments and the like. Unit dosage ranging from about 1 to 250 milligrams per kilogram of body weight of the mammalian recipient are employed. Appropriate pharmaceutical carriers comprise both solids and liquids such as corn starch, lactose, calcium phosphate, stearic acid, polyethylene glycol, water, sesame seed oil, peanut oil, propylene glycol, and so on.

Effective analeptic and analgesic responses are induced in mammals when the compounds of the present invention are administered systemically in an effective dosage ranging from about 1 to 250 milligrams per kilogram body weight of the mammal. Particularly preferred forms of systemic administration are oral, parenteral, and rectal. Examples of parenteral administration are intramuscular, intravenous, and subcutaneous administration. It will be recognized by those skilled in the art that the dosage of the compounds of the present invention will vary with the form and mode of administration and to some degree with the particular compound chosen. It will generally be found that when a compound of the present invention is administered orally, a larger quantity of the active agent is required to produce the same effect as a smaller quantity thereof given parenterally. In general, the compounds of this invention are most desirably administered at a concentration level that will generally afford effective results without causing any harmful or deleterious side effects. A dosage level that is in the range of from about 2.5 to 150 mg./kg. of body weight of the mammalian species treated per day is most preferred in order to achieve effective results.

The compounds of the present invention which are represented by Formula IV are prepared by reaction of a substituted indoline of Formula II with a carboxamide of Formula III in the presence of phosphorus oxychloride as illustrated in the following equation.

lactams, symmetrical and unsymmetrical ureas, or hydrazides.

In carrying out the process of this invention for the preparation of Formula IV compounds approximately equivalent molar quantities of the reactants (indoline and the appropriate carboxamide) and phosphorus oxychloride are dissolved or suspended in an inert solvent. A preferred solvent for carrying out the process is 1,2-dichloroethane, although it may be carried out with other inert solvents such as chloroform, carbon tetrachloride, 1,1-dichloroethane, benzene, toluene, hexane, and the like. The mode of addition of the reactants is not critical in carrying out the hereinabove described process. For example, a solution or suspension of an indoline and a carboxamide can be added to a solution of phosphorus oxychloride or the sequence of addition may be reversed and a solution of phosphorus oxychloride can be added to a solution or suspension of the carboxamide and amine. Alternatively, phosphorus oxychloride can be first added to the amine and the carboxamide then added or the phosphorus oxychloride can be added to the carboxamide and this mixture then combined with the amine. Combination of the reactants provides an exothermic reaction and accordingly external cooling is employed in some instance to moderate the reaction. The reaction takes place in a facile manner when the reactants are combined and generally does not require prolonged reaction periods for completion and formation of an indoline 1-iminomethyl derivative of Formula IV. Generally it is preferred to carry out the reaction with efficient stirring and for periods ranging from about 1 to 18 hours. Reaction may be carried out at temperatures of about −35°C. to 100°C. However, for ease of laboratory operation, it is preferred to carry out the combination of the reactants at room temperature and to then stir the reaction mixture overnight before isolating the product. In some instances, where the carboxamide has only limited solubility in the reaction solvent, the reaction is carried out at refluxing temperature of the inert solvent. For example, 1-[2-(5,5-dimethyl-1-pyrrolinyl)-]indoline is obtained by refluxing a mixture of 5,5-dimethyl-2-pyrrolidinone suspended in 1,2-dichloroethane containing phosphorus oxychloride and indoline.

The compounds of Formula I wherein the X substituent is amino, $R^1CONH$ or $R^1SO_2NH$ are synthesized by an alternate process. This process comprises reduction of compounds of Formula IV wherein the Y substituent is nitro to the corresponding amino derivatives by standard catalytic or chemical procedures well known to the art. The amino derivatives of Formula I, wherein X is $NH_2$, may then be reacted with lower alkylsulfonyl chlorides or lower alkyoyl halides or their respective anhydrides to provide compounds of Formula I wherein X is $R^1CONH$ and $R^1SO_2NH$.

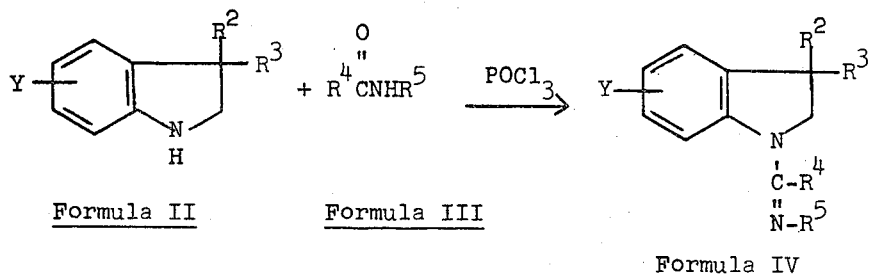

In Formulas II, III, and IV, $R^2$, $R^3$, $R^4$, and $R^5$ have the meanings hereinabove given for Formula I. The Y substituent is selected from the group consisting of hydrogen, nitro and $R^1CO$ wherein $R^1$ represents a lower alkyl group of from 1 to 4 carbon atoms inclusive. Carboxamides of Formula III are comprised of amides,

Pharmacology

The compounds of the present invention effectively stimulate the central nervous system of mammals. Compounds having biological activity of this type are generally referred to as being analeptic agents. Analeptic activity can be demonstrated by the ability of an analeptic agent to antagonize central nervous system depression produced by administration of pentobarbital to cats or chloral hydrate to mice.

The pentobarbital antagonism test for the compounds of the present invention in the cat is carried out in the following fashion. A cat of either sex wherein a chronically indwelling intravenous cannula has been previously surgically inserted, is placed in an observation cubicle measuring 2 ft. × 2ft. × 2ft. The cat is allowed to move about freely at the end of a leash. A dose of 12 milligrams per kilogram of body weight of pentobarbital sodium in aqueous solution is infused at the rate of approximately 2 milligrams per kilogram per minute via tubing contained in the leash. One-half hour after the start of this infusion the cat is in a state of light anesthesia characterized by unconsciousness, immobility, relaxed nictating membrane, and is not responsive to handling but has active pinneal, palpebral and paw-pinch withdrawal reflexes. At this time the 1-iminomethylindoline compound is infused in concentration of 10 milligrams per milliter at a rate of 0.2 milliters per minute until (a) consciousness is restored, (b) a total of 25 milligrams per kilogram of body weight of test compound is administered or (c) mounting toxicity interferes. Consciousness is recognized by the presence of alertness to surroundings as indicated by the ability of the cat's eyes to follow a movement of a nearby object and in its attempts to assume an upright position.

Representative compounds of the present invention wherein a dose of up to 25 milligrams per kilogram of body weight restored consciousness to pentobarbital treated cats are Examples 1–4, 7–10, 12, 15, 17–20, (Table III).

According to the chloral hydrate antagonism test, groups of 20 fasted male albino mice are administered an oral dose of 20 milligrams per kilogram of the 1-iminomethylindoline test compound. This is followed immediately by an intraperitoneal dose of 300 milligrams per kilogram of chloral hydrate. The average reduction in sleeping time compared to a saline-treated control group is a measure of the central nervous system stimulant action of the test compound and is as follows for representative 1-iminomethylindolines of this invention.

TABLE 1

CHLORAL HYDRATE ANTAGONISM IN THE MOUSE

| Example Number (Table III) | Percent Reduction in Sleeping Time at 20 mg/kg Body Weight |
|---|---|
| 2 | 38 |
| 3 | 24 |
| 4 | 24 |
| 7 | 10 |
| 8 | 36 |
| 9 | 65 |
| 17 | 62 |
| 18 | 17 |
| 21 | 50 |

In a number of instances, analeptic activity as shown by antagonism to pentobarbital hypnosis in the cat and chloral hydrate antagonism in the mouse of the present compounds of this invention are equal to or comparative with known central nervous system stimulant agents. For example, 4-ethyl-4-methyl-2,6-piperidinedione (The Merck Index, 8th Edition, page 124), a well known analeptic agent, reduces by 50 percent the sleeping time caused by the administration of a 300 milligram per kilogram of body weight of chloral hydrate to the mouse at a dose of 14.4 milligrams per kilogram body weight. In a comparative test two of the preferred compounds of the present invention, 1-[2-(5,5-dimethyl-1-pyrrolinyl)]indoline hydrochloride and 5-acetyl-1-[2-(1-pyrrolinyl)]indoline, produce a 50 percent reduction of the sleeping time at doses of 15 and 10 milligrams per kilogram of body weight respectively. Comparison of pentobarbital antagonism in cats indicates that 4-ethyl-4-methyl-2,6-piperidinedione and the aforementioned preferred compounds are substantially equiactive in restoring consciousness to a pentobarbital treated cat.

The activity cage technique described by J. W. Kissel, Science, 139, 1224 (1963), was used to measure motor stimulation in rats. In this test, compounds of the present invention such as the analeptic agents 1-[2-(5,5-dimethyl-1-pyrrolinyl)]indoline hydrochloride and 5-acetyl-1-[2-(1-pyrrolinyl)]indoline, did not produce an increase in motor activity. The absence of motor stimulation exhibited by these compounds demonstrates that analeptic action may be present without concomitant motor stimulation. Since motor stimulation is generally associated with analeptic action, the instant compounds of this invention are unique in the respect that while they are analeptic agents they are not motor stimulants.

In addition to having analeptic activity, compounds of Formula I are active agents in preventing the phenylquinone writhing syndrome in mice. The prevention of this syndrome is employed as a measure of analgesic activity — Hendershot and Forsaith, *J. Pharmacol. Exp. Therap.* 125, 237 (1959). In this test, groups of 10 to 20 mice are injected subcutaneously with graduated doses of the test compound. At the time of a predetermined peak effect, the animals are administered a dose of 2.5 milligrams per kilogram of body weight of phenylquinone intraperitoneally. The latter injection induces writhing episodes in the mice. The number of such episodes exhibited by each mouse during the 10 minute period following injection is counted and the average percent of decrease in the number of episodes as compared to a control group of mice is recorded for each dose of test compounds. A log dose-response curve is prepared and the dose of the test compound required to decrease the number of writhing episodes of 50 percent is estimated by interpolation. Results relating to a number of compounds of the present invention compared to aspirin are listed in Table II.

TABLE II

PREVENTION OF PHENYLQUINONE WRITHING

| Example Number (Table III) | $ED_{50}$ mg/kg body weight |
|---|---|
| Aspirin | 20.0 |
| 1 | 21.8 |
| 3 | 15.8 |
| 7 | 3.85 |
| 8 | 13.0 |
| 10 | 5.7 |
| 11 | 17.1 |
| 12 | 11.3 |

TABLE II-continued

PREVENTION OF PHENYLQUINONE WRITHING

| Example Number (Table III) | $ED_{50}$ mg/kg body weight |
|---|---|
| 13 | 33.2 |
| 17 | 7.7 |
| 18 | 16.2 |
| 19 | 10.3 |

DESCRIPTION OF THE PREFERRED EMBODIMENTS

The following examples are intended to illustrate the present invention without limiting it thereto.

EXAMPLES 1–21

General procedure for the preparation of 1-iminomethylindolines

A mixture of equimolar amounts of an indoline and the appropriate carboxamide in 1,2-dichloroethane (250 ml. per 0.1 mole of reactant) is treated dropwise with an equimolar solution of phosphorus oxychloride in a 1,2-dichloroethane (50 ml. per 0.1 mole of reactant ) over a period of 30 minutes to 1 hour at 20°–30°C. The mixture is stirred overnight and then poured into crushed ice.

The dichloroethane layer is separated from the aqueous layer and extracted with dilute hydrochloric acid. A 20% sodium hydroxide solution is added to the dilute acid solution providing an oil or a precipitate which is taken up in ether. Concentration of the ethereal extract provides the crude product which is purified by standard organic procedures well known to those skilled in the art such as by crystallization, distillation, or preparation of a suitable acid addition salt.

The following tabulation is illustrative of a number of 1-iminomethylindolines of the present invention prepared by following the hereinabove described procedure. Purification solvents, melting points, analytical data and infrared absorption spectrum are also provided in Table III.

TABLE III

1-Iminomethylindolines

| Example Number | Product | Starting Materials Amine | Carboxamide |
|---|---|---|---|
| 1 | 1-[(Methylimino)methyl]indoline hydrochloride | Indoline | N-Methylformamide |
| 2 | 1-[(Isopropylimino)methyl]indoline hydrochloride hemihydrate | Indoline | N-Isopropylformamide |
| 3 | 1-[1-(Methylimino)ethyl]indoline hydrochloride | Indoline | N-Methylacetamide |
| 4 | 1-(N,N'-Dimethylamidino)indoline | Indoline | N,N'-Dimethylurea |
| 5 | 1-[(Dimethylhydrazono)methyl]indoline hydrochloride | Indoline | 1-Formyl-2,2-dimethyl hydrazine |
| 6 | 1-[(Cyclohexylimino)methyl]indoline hydrochloride | Indoline | N-Cyclohexylformamide |
| 7 | 1-[2-(1-Pyrrolinyl)]indoline hydrochloride | Indoline | 2-Pyrrolidinone |
| 8 | 1-[2-(5-Methyl-1-pyrrolinyl)]indoline hydrochloride | Indoline | 5-Methyl-2-pyrrolidinone |
| 9 | 1-[2-(5,5-Dimethyl-1-pyrrolinyl)]-indoline hydrochloride | Indoline | 5,5-Dimethyl-2-pyrrolidinone |
| 10 | 1-(3,4,5,6-Tetrahydro-2-pyridyl)-indoline hydrochloride | Indoline | 2-Piperidone |

| Example Number | M.P. (°C.) (Corr.) | Crystallization Solvent | Analysis Calcd. | | Found | | Infrared Absorption (0.5% KBr) Microns |
|---|---|---|---|---|---|---|---|
| 1 | 282–283 | Ethanol | C | 61.06 | C | 61.10 | 2.97, 3.35, 3.43, 5.96, 6.30, |
|   |         |         | H | 6.66  | H | 6.57  | 6.63, 6.79, 6.83, 7.00, 7.29, |
|   |         |         | N | 14.25 | N | 14.06 | 7.84, 8.19, 8.79, 9.20, 9.51, |
|   |         |         | Cl | 18.03 | Cl | 18.11 | 13.15. |
| 2 | 213.5–215 | Ethanol-ether | C | 61.66 | C | 62.21 | 2.90, 3.30, 3.42, 5.80, 6.30, |
|   |           |               | H | 7.76  | H | 7.57  | 6.65, 6.90, 7.25, 7.87, 8.20, |
|   |           |               | N | 11.99 | N | 12.13 | 8.79, 9.75, 9.85, 13.50, |
|   |           |               | Cl | 15.17 | Cl | 15.29 | 19.80 |
| 3 | 228.5–230.5 | Ethanol-ether | C | 62.70 | C | 62.97 | 2.90, 3.32, 6.17, 6.30, 6.60, |
|   |             |               | H | 7.17  | H | 7.15  | 6.85, 7.15, 7.30, 7.40, 7.50, |
|   |             |               | N | 13.30 | N | 13.22 | 7.95, 8.50, 8.80, 9.15, 9.55, |
|   |             |               | Cl | 16.83 | Cl | 16.58 | 13.00. |
| 4 | 142–143 | n-Neptane | C | 69.81 | C | 69.94 | 2.92, 3.15, 3.40, 3.50, 6.15, |
|   |         |           | H | 7.99  | H | 8.01  | 6.71, 6.95, 7.14, 7.29, 7.95, |
|   |         |           | N | 22.20 | N | 22.49 | 8.48, 8.66, 9.50, 9.65, 11.45, 13.32, 15.00. |
| 5 | 179–182.5 | Ethanol | C | 58.53 | C | 58.42 | 2.93, 3.35, 3.42, 3.98, 4.15, |
|   |           |         | H | 7.15  | H | 7.22  | 6.20, 6.35, 6.75, 6.92, 7.18, |
|   |           |         | N | 18.62 | N | 18.56 | 7.59, 7.95, 8.21, 8.50, 8.65, |
|   |           |         | Cl | 15.70 | Cl | 15.66 | 9.75, 10.20, 10.75, 11.40, 12.00, 13.40. |
| 6 | 221–222 | Ethanol-ether | C | 68.03 | C | 68.30 | 2.93, 3.14, 3.30, 3.44, 3.52, |
|   |         |               | H | 8.00  | H | 8.01  | 5.85, 6.30, 6.66, 6.84, 7.22, |
|   |         |               | N | 10.58 | N | 10.56 | 7.89, 8.06, 8.75, 9.25, 9.75, |
|   |         |               | Cl | 13.39 | Cl | 13.67 | 11.25, 13.20. |
| 7 | 265–266.5 | Ethanol-ether | C | 64.71 | C | 64.60 | 2.95, 3.40, 3.60, 6.10, 6.30, |
|   |           |               | H | 6.79  | H | 6.56  | 6.67, 6.89, 7.09, 7.30, 7.69, |
|   |           |               | N | 12.58 | N | 12.34 | 7.92, 8.55, 9.39, 9.50, 9.75, |
|   |           |               | Cl | 15.92 | Cl | 15.78 | 10.84, 13.10. |
| 8 | 212–214 | Ethanol-ether | C | 65.95 | C | 65.75 | 3.40, 3.58, 6.10, 6.68, 6.80, |
|   |         |               | H | 7.24  | H | 7.22  | 7.08, 7.29, 7.80, 7.92, 8.15, |

TABLE III-continued

| Example Number | M.P. (°C.) (Corr.) | Crystallization Solvent | Analysis Calcd. | | Found | | Infrared Absorption (0.5% KBr) Microns |
|---|---|---|---|---|---|---|---|
| | | | N | 11.83 | N | 12.00 | 8.52, 9.10, 9.40, 13.20. |
| | | | Cl | 14.98 | Cl | 14.76 | |
| 9 | 250–251 | Ethanol-ether | C | 67.05 | C | 67.08 | 2.95, 3.40, 6.10, 6.30, 6.68, |
| | | | H | 7.64 | H | 7.62 | 6.80, 6.89, 7.05, 7.30, 7.68, |
| | | | N | 11.17 | N | 11.12 | 7.95, 8.15, 8.54, 8.80, 9.52, |
| | | | Cl | 14.14 | Cl | 14.30 | 9.90, 10.70, 11.92, 13.10, 13.45, 14.30. |
| 10 | 233.5–235.5 | Ethanol-ether | C | 65.95 | C | 65.66 | 2.92, 3.35, 3.40, 6.18, 6.30, |
| | | | H | 7.24 | H | 6.95 | 6.68, 6.88, 7.40, 7.52, 7.90, |
| | | | N | 11.83 | N | 11.65 | 8.20, 8.50, 8.95, 9.29, 9.58, |
| | | | Cl | 14.98 | Cl | 15.03 | 13.18. |

| Example Number | Product | Starting Materials | |
|---|---|---|---|
| | | Amine | Carboxamide |
| 11 | 1-[7-(3,4,5,6-Tetrahydro-2H-azepinyl)]-indoline hydrochloride | Indoline | 2-Oxohexamethylenimine |
| 12 | 1-[5,6-Dihydro-3-(2H-thiazinyl)]indoline hydrochloride | Indoline | 3-Thiomorpholinone |
| 13 | 1-(2-Imidazolin-2-yl)indoline hydrochloride | Indoline | 2-Imidozolinone |
| 14 | 1-[(Piperidinoimino)methyl]indoline hydrochloride | Indoline | N-(1-Piperidinyl)-formamide |
| 15 | 1-(3H-Indol-2-yl)indoline hydrochloride | Indoline | 2-Oxindole |
| 16 | 5-Acetyl-1-(methyliminomethyl)-indoline | 5-Acetylindoline | N-Methylformamide |
| 17 | 5-Acetyl-1-[2-(1-pyrrolinyl)]indoline | 5-Acetylindoline | 2-Pyrrolidinone |
| 18 | 5-Acetyl-1-[7-(3,4,5,6-tetrahydro-2H-azepinyl)]indoline hydrochloride | 5-Acetylindoline | 2-Oxohexamethylenimine |
| 19 | 1-[(Methylimino)methyl]-5-nitro-indoline hydrochloride | 5-Nitroindoline | N-Methylformamide |
| 20 | 5-Nitro-1-[2-(1-pyrrolinyl)]indoline hydrochloride | 5-Nitroindoline | 2-Pyrrolidinone |
| 21 | 1-[7-(3,4,5,6-Tetrahydro-2H-azepinyl)]-5-nitroindoline hydrochloride | 5-Nitroindoline | 2-Oxohexamethylenimine |

| Example Number | M.P. (°C.) (Corr.) | Crystallization Solvent | Analysis Calcd. | | Found | | Infrared Absorption (0.5% KBr) Microns |
|---|---|---|---|---|---|---|---|
| 11 | 224–226 (dec.) | Ethanol-ether | C | 67.05 | C | 66.77 | 2.95, 3.38, 3.48, 6.19, 6.30, |
| | | | H | 7.64 | H | 7.52 | 6.65, 6.85, 7.30, 7.48, 7.90, |
| | | | N | 11.17 | N | 10.89 | 8.22, 8.60, 8.95, 10.15, |
| | | | Cl | 14.14 | Cl | 14.23 | 11.50, 11.85, 13.15. |
| 12 | 199–201.5 | Ethanol-ether | C | 56.57 | C | 56.59 | 2.90, 3.40, 3.52, 6.15, 6.30, |
| | | | H | 5.93 | H | 6.17 | 6.70, 6.90, 7.44, 7.94, 8.50, |
| | | | N | 11.00 | N | 11.15 | 9.15, 13.09. |
| | | | Cl | 13.91 | Cl | 14.02 | |
| 13 | 325–327.5 (dec.) | Ethanol | C | 59.06 | C | 59.26 | 3.21, 6.10, 6.30, 6.49, 6.70, |
| | | | N | 6.31 | H | 6.24 | 6.81, 7.05, 7.29, 7.79, 7.91, |
| | | | N | 18.78 | N | 18.99 | 8.38, 9.22, 9.40, 9.67, 10.60, |
| | | | Cl | 15.85 | Cl | 15.93 | 11.56, 13.15. |
| 14 | 200–201 | Ethanol | C | 63.27 | C | 63.31 | 2.90, 3.44, 3.86, 6.20, 6.35, |
| | | | H | 7.58 | H | 7.63 | 6.70, 6.90, 7.15, 7.35, 7.50, |
| | | | N | 15.81 | N | 15.69 | 7.96, 8.40, 9.00, 9.80, 10.65, |
| | | | Cl | 13.34 | Cl | 13.57 | 11.75, 13.20. |
| 15 | 268.5–271 (dec.) | Ethanol-ether | C | 70.97 | C | 71.09 | 2.95, 3.30, 3.45, 6.10, 6.32, |
| | | | H | 5.58 | H | 5.52 | 6.85, 7.10, 7.30, 7.60, 8.35, |
| | | | N | 10.35 | N | 10.21 | 9.25, 9.75, 11.80, 13.40. |
| | | | Cl | 13.10 | Cl | 12.63 | |
| 16 | 118–120 | Ethanol | C | 71.26 | C | 71.15 | 3.45, 3.60, 6.05, 6.25, 6.62, |
| | | | H | 6.98 | H | 7.02 | 6.90, 7.10, 7.36, 7.49, 7.62, |
| | | | N | 13.85 | N | 13.81 | 7.80, 8.28, 8.92, 9.50, 10.02, 10.35, 11.05, 12.38, 13.85, 14.05. |
| 17 | 124.5–126 | Isopropyl ether | C | 73.65 | C | 73.37 | 2.95, 3.55, 6.00, 6.19, 6.31, |
| | | | H | 7.07 | H | 6.93 | 6.70, 6.95, 7.10, 7.20, 7.36, |
| | | | N | 12.27 | H | 12.35 | 7.50, 7.90, 8.63, 9.15, 10.50, 11.29, 11.82. |
| 18 | 250.5–252.5 | Ether | C | 65.63 | C | 65.47 | 2.99, 3.40, 3.49, 6.00, 6.20, |
| | | | H | 7.23 | H | 7.33 | 6.39, 6.70, 6.80, 6.95, 7.40, |
| | | | N | 9.57 | N | 9.43 | 7.75, 7.94, 8.42, 8.54, 9.10, |
| | | | Cl | 12.10 | Cl | 11.80 | 9.50, 10.20, 10.54, 11.95, 13.20, 14.20. |
| 19 | 244–246.5 (dec.) | Ether | C | 49.70 | C | 49.41 | 2.96, 3.45, 5.95, 6.30, 6.56, |
| | | | H | 5.00 | H | 5.12 | 6.82, 7.33, 7.50, 7.83, 8.49, |
| | | | N | 17.39 | N | 17.12 | 8.78, 9.16, 9.50, 10.90, |
| | | | Cl | 14.67 | Cl | 14.37 | 12.27, 13.50. |
| 20 | 281–282 (dec.) | Ether | C | 53.84 | C | 54.06 | 2.96, 3.40, 6.09, 6.30, 6.70, |
| | | | H | 5.27 | H | 5.24 | 7.00, 7.45, 7.69, 7.92, 8.60, |
| | | | N | 15.70 | N | 15.83 | 9.29, 9.42, 10.95, 11.95, |
| | | | Cl | 13.25 | Cl | 13.28 | 12.28, 13.00. |
| 21 | 268.5–270.5 | Ether | C | 56.85 | C | 56.94 | 2.95, 3.40, 3.52, 6.15, 6.30, |
| | | | H | 6.13 | H | 6.32 | 6.75, 6.95, 7.45, 7.87, 8.40, |
| | | | N | 14.21 | N | 14.15 | 8.65, 9.50, 10.20, 10.90, |
| | | | Cl | 11.99 | Cl | 11.91 | 11.20, 13.40. |

EXAMPLE 22

5-Amino-1-[2-(1-pyrrolinyl)]indoline

A solution of 1-[2-(1-pyrrolinyl)]-5-nitroindoline (8 g. 0.03 mole) in 200 ml. of 0.15 N hydrochloric acid is reduced on a Parr hydrogenator employing 1 teaspoon of W-60 Raney Nickel catalyst. When the hydrogen uptake ceases the catalyst is collected and the filtrate is made basic with 20% potassium hydroxide solution which provides a precipitate of the free amine. The precipitate is taken up in 50 ml. of acetone, treated with decolorizing charcoal and concentrated to about 20 ml. On standing, the acetone solution deposits 1.6 g. (27%) of 1-[2-(1-pyrrolinyl)]-5-aminoindoline, m.p. 174°–176.5°C.

Analysis. Calcd. for $C_{12}H_{15}N_3$: C, 71.61; H, 7.51; N, 20.88. Found: C, 71.46; H, 7.76; N, 20.59.

EXAMPLE 23

5-Methanesulfonamido-1-[2-(1-pyrrolinyl)]-indoline

An equimolar portion of methanesulfonyl chloride is added to 5-amino-1-[2-(1-pyrrolinyl)]indoline in pyridine. After stirring the mixture overnight the product is isolated by quenching the pyridine solution in water and collecting the precipitated 5-methanesulfonamido-1-[2-(1-pyrrolinyl)]indoline. Alternatively, the product may be recovered by extraction with a water immiscible organic solvent such as ether, benzene, ethyl acetate and the like.

EXAMPLE 24

5-Butyramido-1-[2-(1-pyrrolinyl)]indoline

Following the procedure of Example 23, an equimolar portion of butuyryl chloride is added to 5-amino-1-[2-(1-pyrrolinyl)]indoline in pyridine to provide the butuyramido derivative.

EXAMPLES 25 – 48

The procedures described for Examples 1 through 24 are followed to obtain additional products of the present invention as listed in Table IV. For each example the starting reactants are given.

TABLE IV

ADDITIONAL 1-IMINOMETHYLINDOLINES

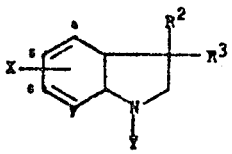

| Example Number | X | R² | R³ | Y | Starting Materials |
|---|---|---|---|---|---|
| 25 | H | H | CH₃ | pyrrolinyl | 3-Methylindoline and 2-pyrrolidinone |
| 26 | H | H | C₂H₅ | —C—CH₃ / N—CH₃ | 3-Ethylindoline and N-methylacetamide |
| 27 | H | H | CH(CH₃)₂ | 5,5-dimethylpyrrolinyl | 3-Isopropylindoline and 5,5-dimethyl-2-pyrrolidinone |
| 28 | H | CH₃ | CH₃ | 5,5-dimethylpyrrolinyl | 3,3-Dimethylindoline and 5,5-dimethyl-2-pyrrolidinone |
| 29 | H | n—C₃H₇ | n—C₃H₇ | pyrrolinyl | 3,3-Dipropylindoline and 2-pyrrolidinone |
| 30 | 5—NO₂ | H | H | azabicyclooctenyl | 5-Nitroindoline and 2-azabicyclo[2.2.2]octan-3-one |
| 31 | 6—NO₂ | H | H | 5,5-dimethylpyrrolinyl | 6-Nitroindoline and 5,5-dimethyl-2-pyrrolidinone |
| 32 | 5—NO₂ | CH₃ | CH₃ | 5,5-dimethylpyrrolinyl | 3,3-Dimethyl-5-nitroindoline and 5,5-dimethyl-2-pyrrolidinone |
| 33 | 6—NH₂ | H | H | morpholinyl | 6-Nitroindoline and 3-ketomorpholine |
| 34 | 5—n—C₄H₉SO₂NH | CH₃ | CH₃ | pyrrolinyl | 3,3-Dimethyl-5-nitroindole and 2-pyrrolidinone |

TABLE IV-continued
ADDITIONAL 1-IMINOMETHYLINDOLINES

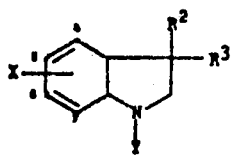

| Example Number | X | R² | Product R³ | Y | Starting Materials |
|---|---|---|---|---|---|
| 35 | 5—CH₃C(O) | CH₃ | CH₃ | pyrrolinyl | 3,3-Dimethyl-5-acetylindoline and 2-pyrrolidinone |
| 36 | H | H | H | —CH=N-cyclobutyl | Indoline and N-cyclobutylformamide |
| 37 | H | H | H | —C(=n-C₃H₇)-cycloheptyl | Indoline and N-cycloheptylbutyramide |
| 38 | H | H | H | —C(=N—CH(CH₃)₂)—NHCH(CH₃)₂ | Indoline and N,N'-diisopropylurea |
| 39 | H | H | H | —C(=N—CH(CH₃)₂)—NHCH₃ | Indoline and N-isopropyl-N'-methylurea |
| 40 | H | H | H | C(—CH₃)=N,N(CH₃)(n-C₃H₇) | Indoline and 1-acetyl-2-methyl-2-propylhydrazine |
| 41 | H | H | H | 4-CH₃-pyrrolinyl | Indoline and 4-methyl-2-pyrrolidinone |
| 42 | H | H | H | 3-CH₃-pyrrolinyl | Indoline and 3-methyl-2-pyrrolidinone |
| 43 | 5—n—C₃H₇C(O) | H | H | 5,5-(CH₃)₂-pyrrolinyl | 5-Butyrylindoline and 5,5-dimethyl-2-pyrrolidinone |
| 44 | 5—(CH₃)₂CHC(O) | H | H | pyrrolinyl | 5-Isobutyrylindoline and 2-pyrrolidinone |
| 45 | 6—CH₃C(O) | H | H | pyrrolinyl | 6-Acetylindoline and 2-pyrrolidinone |
| 46 | 5—CH₃C(O)NH | H | H | 5,5-(CH₃)₂-pyrrolinyl | 5-Nitroindoline and 5,5-dimethyl-2-pyrrolidinone |
| 47 | 6—CH₃C(O)NH | H | H | pyrrolinyl | 6-Nitroindoline and 2-pyrrolidinone |
| 48 | 5—(CH₃)₂CHCH₂C(O)NH | H | H | pyrrolinyl | 5-Nitroindoline and 2-pyrrolidinone |

EXAMPLE 49
Tablets

The iminomethylindolines compounds of the present invention are compounded into tablets according to the following example.

| Material | Amount |
|---|---|
| 1-[2-(5,5-dimethyl-1-pyrrolinyl)]indoline hydrochloride | 58.0 g. |
| Magnesium stearate | 1.3 g. |
| Corn starch | 12.4 g. |
| Corn starch pregelatinized | 1.3 g. |
| Lactose | 185.0 g. |

The foregoing materials are blended in a twin-shell blender and then granulated and pressed into tablets weighing 258 mg. each. Each tablet contains 50 mg. of active ingredient.

EXAMPLE 50
Solution for Parenteral Injection

The 1-iminomethylindoline compounds of the present invention are formulated for parenteral administration according to the following example. A sterile solution suitable for intravenous injection is prepared by dissolving 20 g. of 1-[2-(5,5-dimethyl-1-pyrrolinyl)]indoline hydrochloride in 2 liters of water for injection, USP. The solution is adjusted to pH 4.2 with 0.1 N sodium hydroxide. The solution is sterilized by passage through a bacteriological filter and aseptically filled into 10 ml. glass ampoules, each ampoule contains 50 mg. of active ingredient.

What is claimed is:

1. A compound selected from the group consisting of indoline bases having the formula

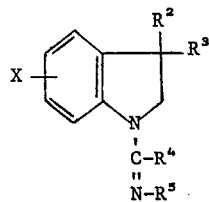

and the pharmaceutically acceptable acid addition salts thereof wherein

X is located in any of the 4, 5, 6, or 7 positions of the indoline ring and is selected from the group consisting of hydrogen, nitro, amino, $R^1CO$, $R^1CONH$, and $R_1SO_2NH$ wherein $R^1$ is lower alkyl group of from 1 to 4 carbon atoms inclusive, $R^2$ and $R^3$ are independently selected from the group consisting of hydrogen and lower alkyl of from 1 to 3 carbon atoms inclusive, and $R^4$ and $R^5$ are joined to form in combination with the atoms to which they are attached a 5,6-dihydro-3-(2H-thiazinyl), 2-imidazolin-2-yl, or 3H-indol-2-yl group.

2. The compound of claim 1, 1-[5,6-dihydro-3-(2H-thiazinyl)]indoline, or a pharmaceutically acceptable acid addition salt thereof.

3. The compound of claim 1, 1-(2-imidazolin-2-yl)indoline, or a pharmaceutically acceptable acid addition salt thereof.

4. The compound of claim 1, 1-(3H-indol-2-yl)indoline, or a pharmaceutically acceptable acid addition salt thereof.

* * * * *